(12) United States Patent
Morel et al.

(10) Patent No.: US 7,628,370 B2
(45) Date of Patent: Dec. 8, 2009

(54) MOUNTING INTERFACE SYSTEMS AND METHODS FOR PURPOSES OF TESTING SEAT TRACKS

(75) Inventors: Fabrice Morel, Denton, TX (US); Robert W. Trimble, Gainesville, TX (US); Monique Le Roux, Denton, TX (US); Klay E. Gilbert, Lindsay, TX (US)

(73) Assignee: Weber Aircraft LLC, Gainesville, TX (US)

( * ) Notice: Subject to any disclaimer, the term of this patent is extended or adjusted under 35 U.S.C. 154(b) by 165 days.

(21) Appl. No.: 11/480,789

(22) Filed: Jul. 3, 2006

(65) Prior Publication Data

US 2008/0001050 A1      Jan. 3, 2008

(51) Int. Cl.
*F16M 13/00* (2006.01)
(52) U.S. Cl. .................. 248/419; 248/424; 297/311
(58) Field of Classification Search .................. 248/419, 248/424, 429; 297/344.11, 311, 300; 29/402.01, 29/407.05, 407.09, 407.1
See application file for complete search history.

(56) References Cited

U.S. PATENT DOCUMENTS

| | | | |
|---|---|---|---|
| 1,863,248 A | | 6/1932 | McGrew |
| 1,891,457 A | * | 12/1932 | Stannard ............... 248/429 |
| 3,785,600 A | * | 1/1974 | Padovano ............... 248/188.1 |
| 4,718,719 A | * | 1/1988 | Brennan ............... 297/216.2 |
| 6,086,018 A | * | 7/2000 | Gobeil et al. ........... 244/122 R |
| 6,293,585 B1 | | 9/2001 | Bruns |
| 6,460,818 B1 | * | 10/2002 | Garelick et al. ........... 248/420 |
| 6,959,900 B2 | * | 11/2005 | Hoshihara et al. ......... 248/429 |
| 2005/0156095 A1 | | 7/2005 | Vichniakov |

FOREIGN PATENT DOCUMENTS

| | | |
|---|---|---|
| EP | 0 215 495 | 3/1987 |
| EP | 0 282 244 | 9/1988 |
| JP | 2002 166768 | 6/2002 |

OTHER PUBLICATIONS

"AC 25.562-1B—Subject: Dynamic Evaluation of Seat Restraint Systems and Occupant Protection on Transport Airplanes" Internet Citation [Online] Jan. 10, 2006, XP002451495 Retrieved from the Internet: URL:http//www1.airweb.faa.gov/Regulatory_and_Guidance_Library/rgAdvisory Circular.nsf/0/808324bf7790fda3862571010075bcbf/$FILE/AC25.562-1b.pdf>[retrieved on Sep. 19, 2007] cited in the application.
International Search Report in related Application No. PCT/US2007/015482.
Statement of Applicants in Information Disclosure Statement dated Sep. 5, 2006.

* cited by examiner

*Primary Examiner*—A. Joseph Wujciak, III
(74) *Attorney, Agent, or Firm*—Dean W. Russell; Kilpatrick Stockton LLP

(57) ABSTRACT

Mounting techniques and systems are detailed. Such techniques and systems are particularly, although not necessarily exclusively, useful for connecting vehicle seat tracks to fixtures for dynamic testing. No holes need necessarily penetrate central portions of the base plates of the tracks.

4 Claims, 6 Drawing Sheets

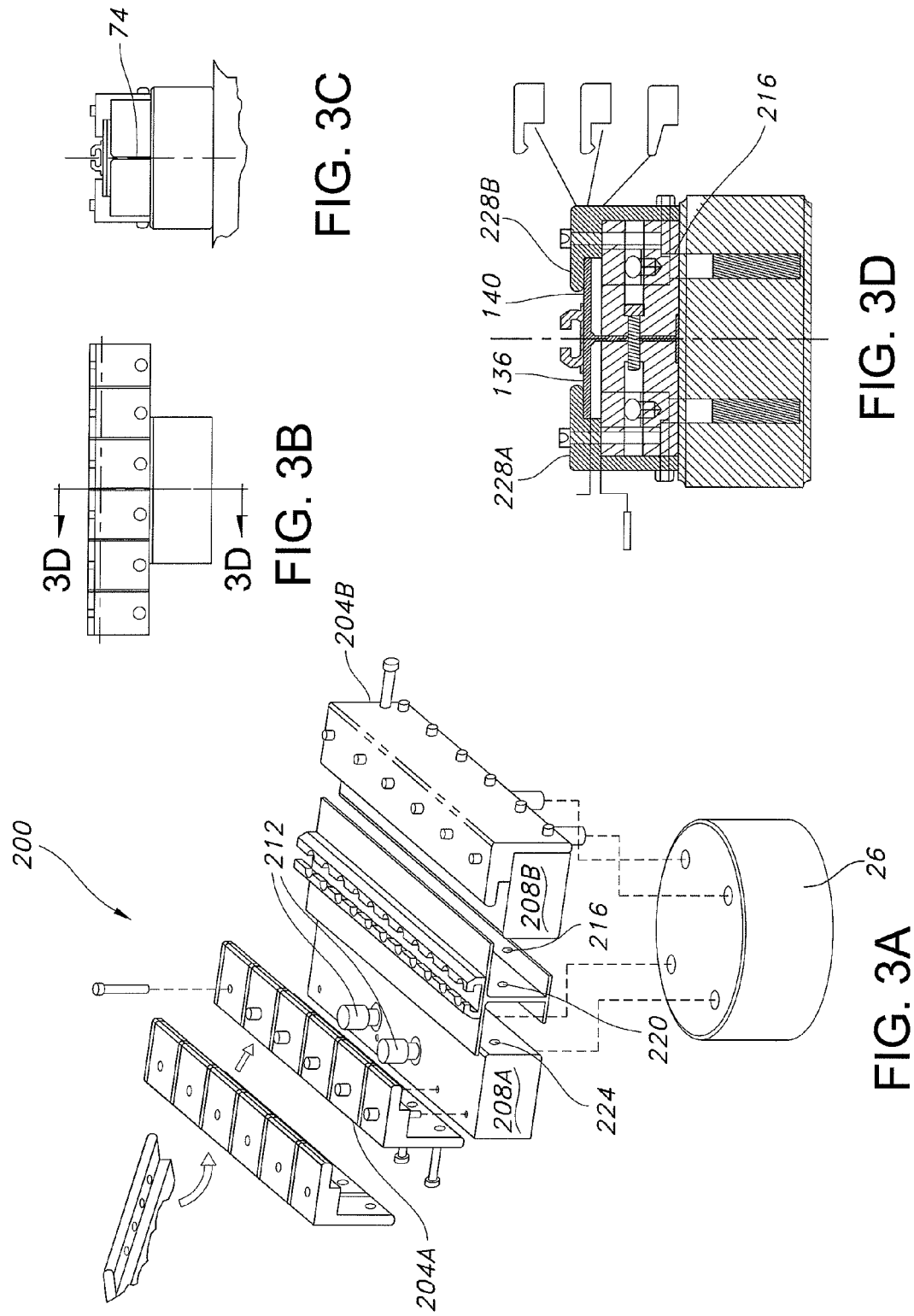

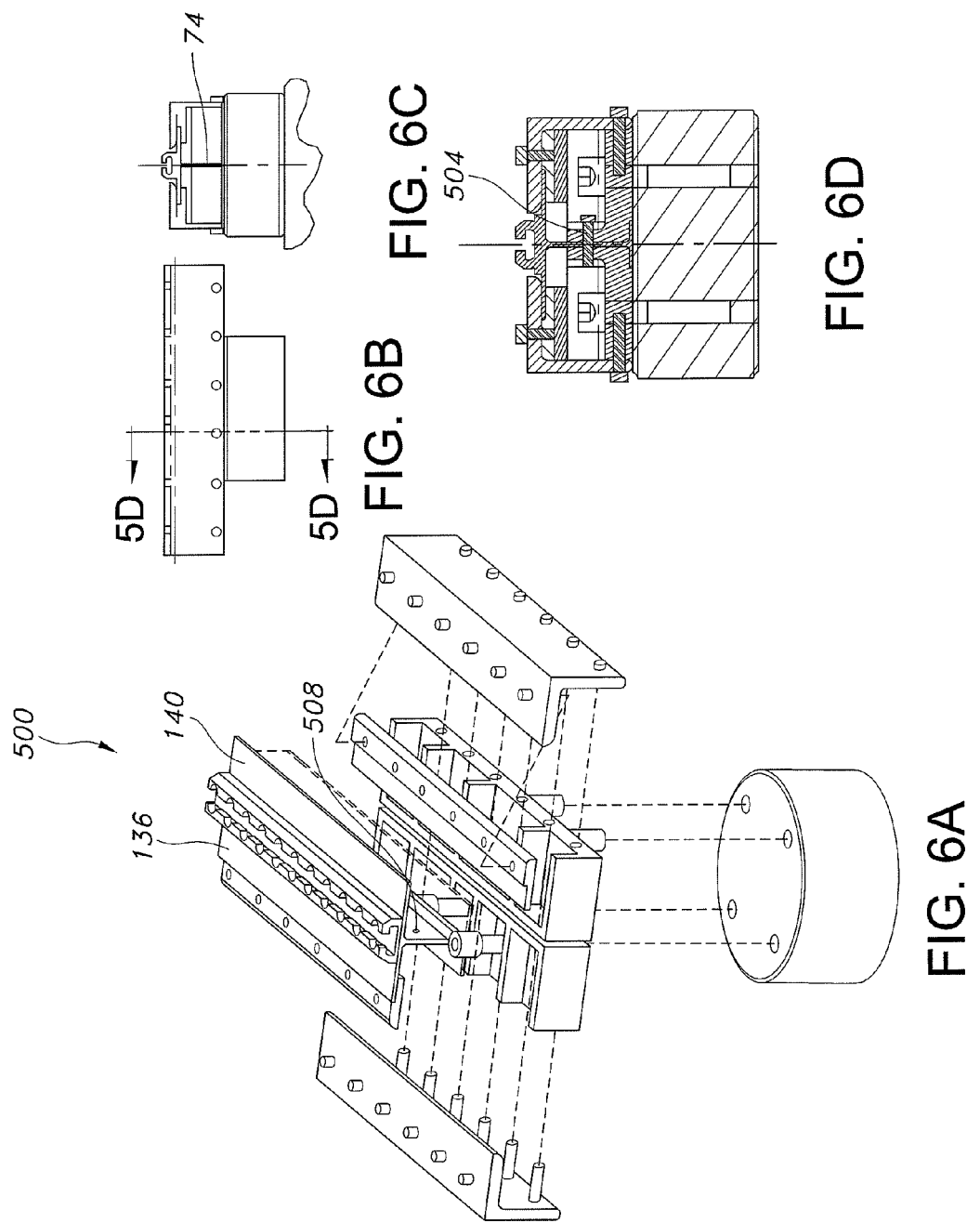

MOUNTING INTERFACE SYSTEMS AND METHODS FOR PURPOSES OF TESTING SEAT TRACKS

FIELD OF THE INVENTION

This invention relates to mechanisms for and methods of mounting objects to test fixtures and more particularly, but not exclusively, to such mechanisms for and methods of mounting aircraft seat tracks to dynamic test fixtures.

BACKGROUND OF THE INVENTION

Federal standards in the United States prescribe characteristics of seat and restraint systems in transport category airplanes during emergency landing conditions. Among requirements of U.S. regulations is that "each seat type design approved for crew or passenger occupancy during takeoff and landing must successfully complete dynamic tests or be demonstrated by rational analysis based on dynamic tests of a similar type seat" pursuant to certain parameters thereafter provided. See 14 C.F.R. § 25.562. Accordingly, sections of tracks to which aircraft seats are connected must be mounted to test fixtures for purposes of performing the required dynamic testing.

Aircraft seat tracks conventionally comprise a horizontally-oriented base plate from which a crown upwardly extends. The base plate is connected to a structural member of the air frame of the aircraft in which it is situated to prevent relative movement of the plate and frame. Passenger or crew seats (or both) are connected to the crowns of the tracks. Such connection may be direct or indirect and need not necessarily be permanent, as many aircraft cabins are reconfigured from time to time.

FIGS. 1A-C illustrate a section of seat track 10 as conventionally used for testing purposes. As is typical, track 10 includes base plate 14 as well as integrally-formed crown 18. Crown 18 extends longitudinally along base plate 14 and is symmetric about a longitudinally-extending center line CL of the plate 14. For conventional testing purposes, also created within track 10 are multiple through holes 22 longitudinally spaced along base plate 14 in the region of crown 18. Holes 22 are centered transversely in base plate 14; i.e. they are aligned with center line CL.

Also detailed in FIG. 1A are load cell 26 and mounting interface 30. Load cell 26 forms part of a dynamic test fixture for seat track 10 pursuant to federal standards. As illustrated, upper surface 34 of load cell 26 typically has circular cross-section with (four) mounting openings 38 spaced ninety degrees about its periphery.

Mounting interface 30 functions to facilitate connection of seat track 10 to load cell 26. Interface 30 conventionally comprises a structure of generally-rectangular cross-section with two sets of openings 42 and 46, one each to match holes 22 and openings 38. Openings 46 extend through interface 30 in alignment with openings 38 of load cell 26. Consequently, bolts or other fasteners may be passed through openings 46 into openings 38 to attach interface 30 to load cell 26.

Openings 42, by contrast, are designed to align with holes 22. They thus are spaced longitudinally in a central region 50 of interface 30 and accept bolts 54 (or other fasteners) passed through holes 22 to connect track 10 and interface 30. Because bolts 54 do not extend into load cell 26, openings 42 need not necessarily extend the full depth of interface 30.

At least a substantial portion of upper surface 58 of interface 30, as well as lower surface 62 of base plate 14, are flat, so that most or all of upper surface 58 is available to support the plate 14 when interface 30 and plate 14 are connected. Likewise, both lower surface 66 of interface 30 and upper surface 34 of load cell 26 are flat. Accordingly, interface 30 and plate 14 readily rest upon load cell 26 during testing.

In some cases it may be beneficial to test seat tracks more representative of those actually installed in aircraft. FIGS. 2A-B depict, among other things, one such seat track 70. Like seat track 10, track 70 includes a (flat) base plate 14. Track 70 additionally comprises an integrally-formed crown 18 extending longitudinally therealong and which is symmetric about a longitudinally-extending center line CL of the plate 14. Unlike track 10, seat track 70 also includes a vertical member 74 extending downward from plate 14 along center line CL, thus assuming a "T" shape in cross-section. Alternatively, seat track 70 may include both vertical member 74 and a horizontal base member 222 (see, e.g., FIG. 3D) so that it assumes an "I" shape in cross-section.

The presence of vertical member 74 precludes ready attachment of track 70 to interface 30, as lower surface 62 of base plate 14 no longer may abut upper surface 58 of the interface 30. The existence of vertical member 74 thus likewise disrupts creation of holes 22. Accordingly, new mounting techniques and systems must be devised to perform dynamic testing of track 70 to comply with federal regulations.

SUMMARY OF THE INVENTION

The present invention provides such new mounting techniques and systems. It further provides mounting methods and systems in which no holes 22 need necessarily be created in base plate 14. Instead, tracks may be clamped in position pursuant to the current invention, thus effecting attachment of tracks to interfaces in non-destructive manners. Further, to the extent desirable, fastening holes may be created in vertical member 74.

In certain preferred embodiments of the invention, clamping of both the base plate and the vertical member of the track occurs. Additionally, clamping of the base plate may occur twice, on each side of the longitudinal center line. Such clamping of all major surfaces of the track clearly furnishes adequate support for the track when the interface is connected to a fixture for testing.

One embodiment of the invention includes a pair of elongated brackets with generally L-shaped cross-section. A horizontally-oriented leg of each bracket is designed to contact the upper face of the base plate of the track. Each horizontal leg also may include a series of longitudinally-spaced holes through which fasteners may pass. Vertically-oriented legs of the brackets similarly may include series of longitudinally-spaced holes through which fasteners may pass.

Also included in this embodiment of the invention may be two elongated, generally rectangular sections. Such sections are configured to contact the lower face of the base plate of the track and include openings longitudinally aligned with those of the horizontal legs of brackets. Appropriate fasteners passing through the holes of both the horizontal bracket legs and the rectangular sections may cause these components to clamp tightly against the opposed faces of the base plate of the track.

Additionally incorporated into this embodiment of the invention are two clamping members. In use, the clamping members may be connected to the upper face of the load cell and to the vertically-oriented legs of the brackets. Upstanding walls of the clamping members also function to sandwich the vertical member of the track, thus retaining it in an appropriate position for testing.

It thus is an optional, non-exclusive object of the present invention to provide mounting interface systems and methods for purposes of testing seat tracks.

It is also an optional, non-exclusive object of the present invention to provide interface systems and methods relating to tracks on which aircraft or other seats or equipment are mounted.

It is an additional optional, non-exclusive object of the present invention to provide mounting interface systems and methods in which no holes need necessarily penetrate central portions of base plates of the tracks under test.

It is a further optional, non-exclusive object of the present invention to provide mounting interface systems and methods in which seat tracks may be clamped in position for testing.

It is, moreover, an optional, non-exclusive object of the present invention to provide mounting interface systems and methods for use with seat tracks having downwardly-extending vertical members.

It is another optional, non-exclusive object of the present invention to provide mounting interface systems and methods utilizing components such as brackets, rectangular sections, and clamping members.

Other objects, features, and advantages of the present invention will be apparent to those skilled in the relevant fields with reference to the remaining text and drawings of this application.

BRIEF DESCRIPTION OF THE DRAWINGS

FIGS. 3A-D present views of a second embodiment of the seat track mounting assembly of the present invention.

FIGS. 6A-D present views of a fifth embodiment of the seat track mounting assembly of the present invention.

DETAILED DESCRIPTION

Figures 1A, 1B, 1C:
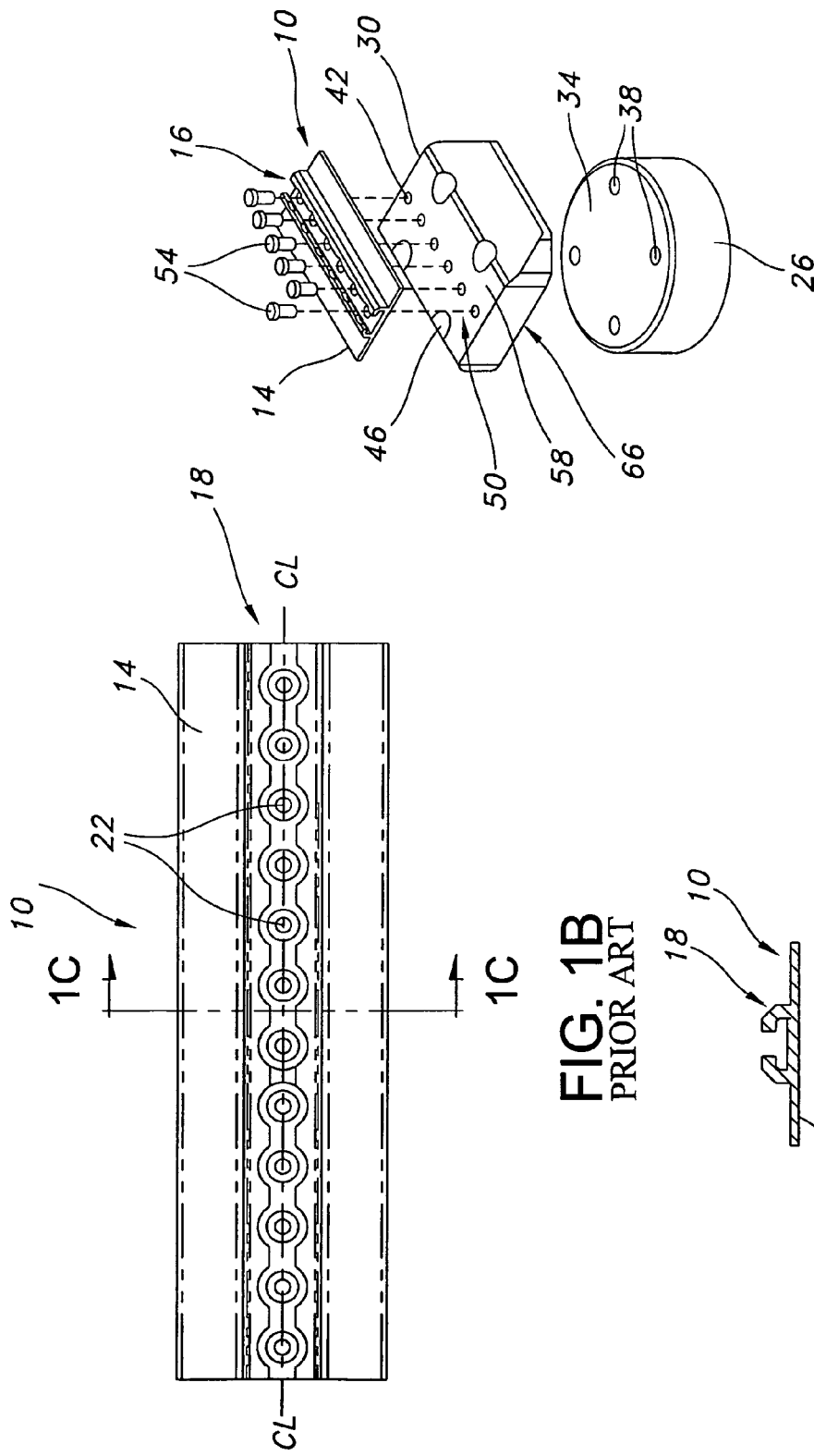
FIG. 1A is an exploded perspective view of components of a conventional seat track mounting assembly.
FIG. 1B is a top plan view of the seat track of FIG. 1A.
FIG. 1C is a front elevational view of the seat track of FIG. 1A.
Figures 2A, 2B:
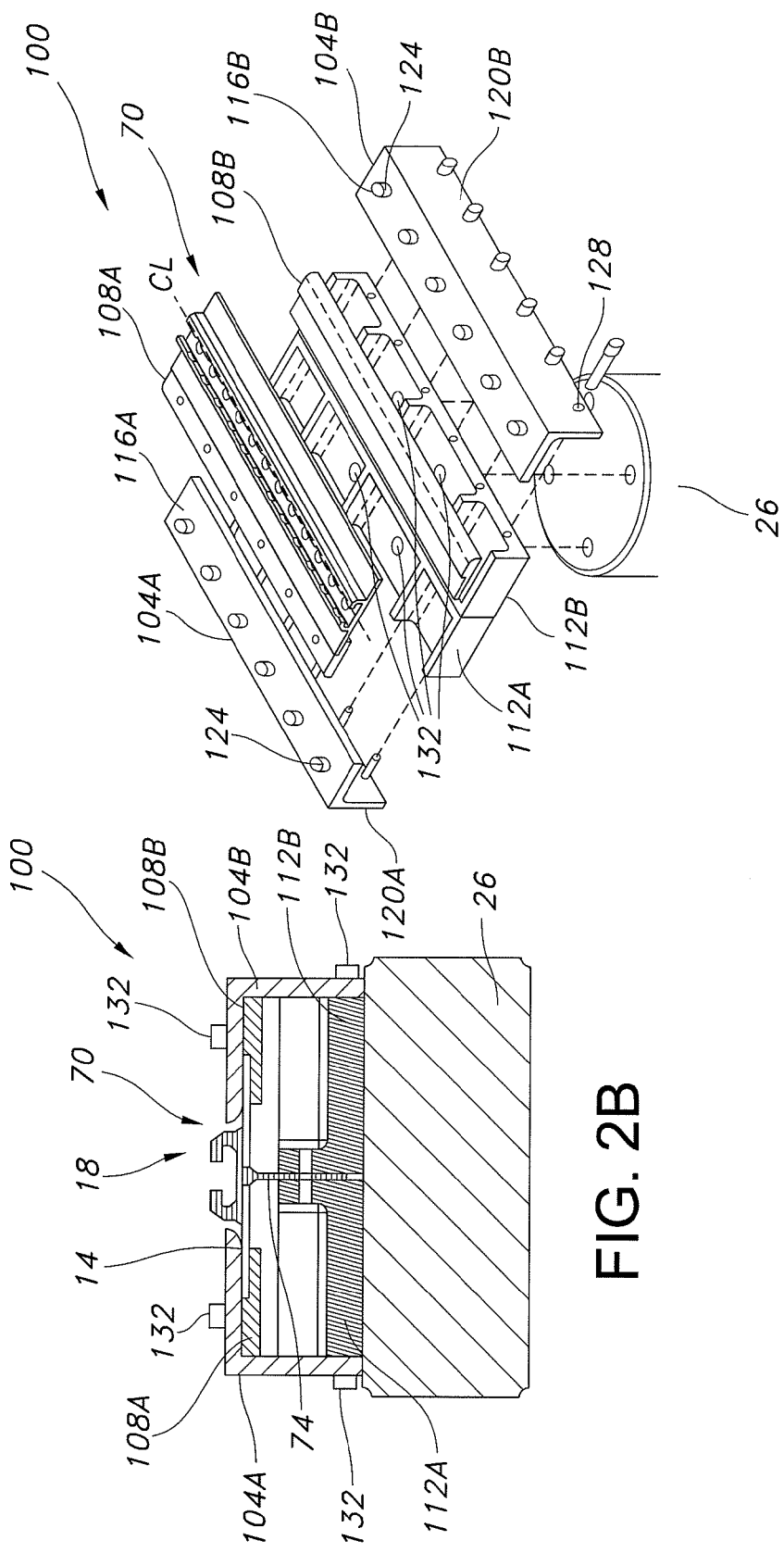
FIG. 2A is an exploded perspective view of components of a seat track mounting assembly of the present invention.
FIG. 2B is a cross-sectional view of the seat track mounting assembly of FIG. 3A.
Figure 4C:
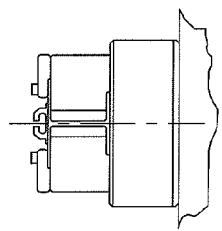
FIGS. 4A-D present views of a third embodiment of the seat track mounting assembly of the present invention.
Figure 4D:
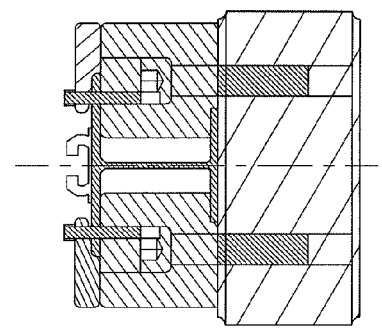
Figure 4B:
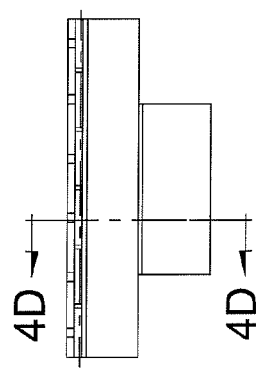
Figure 4A:
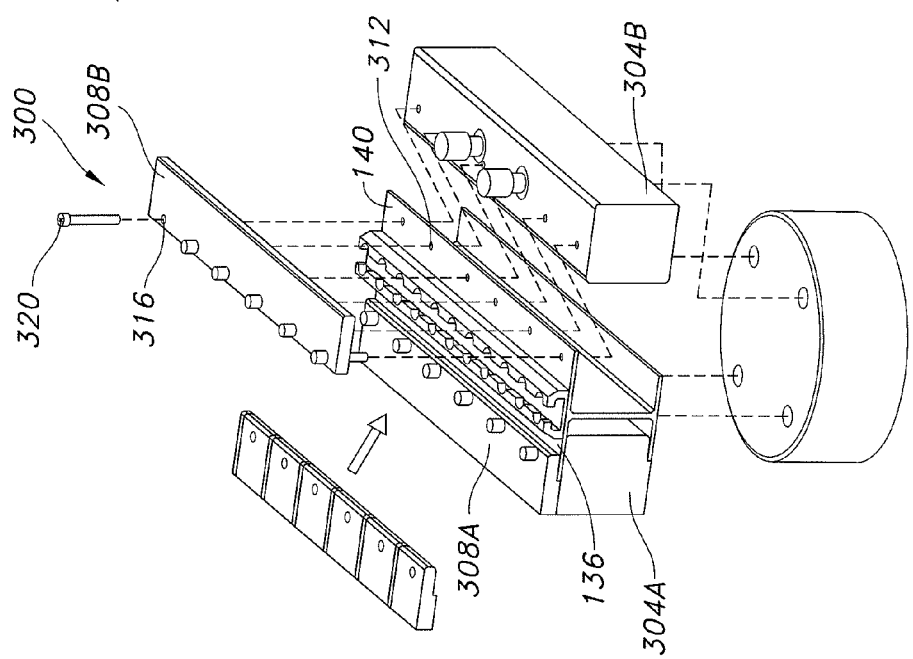
Figure 5C:
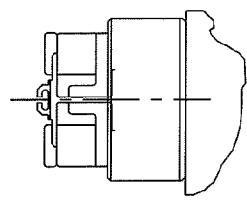
FIGS. 5A-D present views of a fourth embodiment of the seat track mounting assembly of the present invention.
Figure 5B:
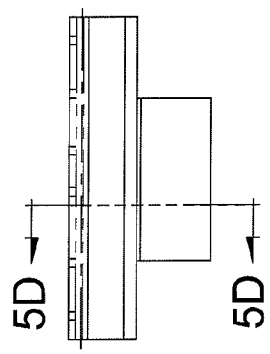
Figure 5D:
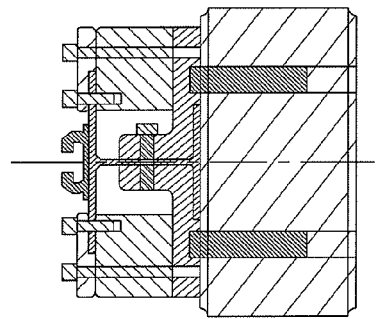
Figure 5A:
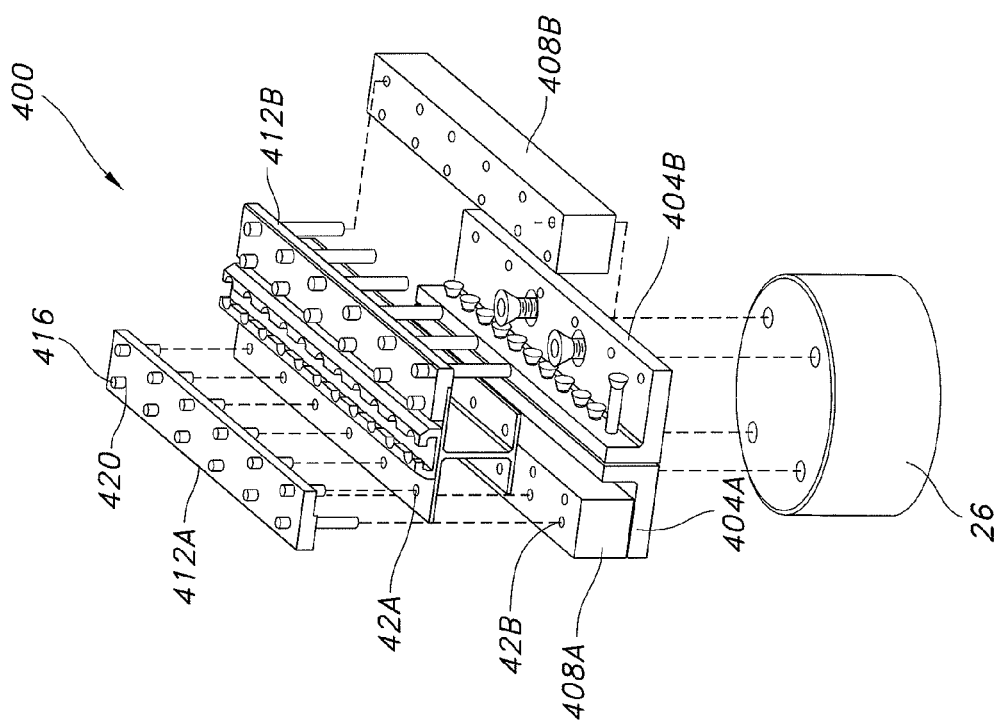

Illustrated in FIGS. 2A-B is mounting system 100. System 100 is configured to function as an interface between a test fixture and an object to be tested. As shown in FIGS. 2A-B, system 100 may connect seat track 70 to load cell 26. However, those skilled in the relevant art will recognize that system 100 may be useful in other situations as well.

An exemplary version of system 100 includes brackets 104A-B, rectangular sections 108A-B, and clamping members 112A-B. These or similar components function to clamp seat track 70 in a suitable position relative to load cell 26. They do so without any need to drill holes in base plate 14 of the track 70, thus avoiding potential structural degradation of the plate 14 during test.

Each of brackets 104A and 104B may comprise two elongated legs, preferably integrally formed at a right angle. Preferred bracket 104A, therefore, may include horizontally-oriented leg 116A and vertically-oriented leg 120A. Bracket 104B, similarly, may comprise horizontally- and vertically-oriented legs 116B and 120B, respectively. One or more holes 124 penetrate each of horizontally-oriented legs 116A-B, while at least one hole 128 penetrates each of vertically-oriented legs 120A-B. Holes 124 and 128 are adapted to receive cap screws or other fasteners 132 during assembly of system 100. Openings 132 in clamping members 112A-B, further, receive fasteners in order to connect system 100 to load cell 26.

Assembly of system 100 is relatively straightforward. Vertical member 74 may be clamped between clamping members 112A-B, which are attached directly to load cell 26. Each of segments 136 and 140 opposite crown 18 of base plate 14 may also be clamped between horizontally-oriented legs 116A and 116B, respectively, and rectangular sections 108A and 108B. Thus, when vertically-oriented legs 120A and 120B are attached to respective clamping members 112A and 112B, seat track 70 is firmly connected to the testing fixture.

FIGS. 3A-6D illustrate alternative assemblies to system 100. System 200, for example, may include brackets 204A-B as well as clamping members 208A-B. Bolts 212 or other fasteners may connect clamping members 208A-B to load cell 26. Further, bolts 216 or other fasteners may extend from clamping member 208B through openings 220 of vertical member 74 into openings 224 of clamping member 208A to secure seat track 70 in place. Brackets 204A-B may attach to respective clamping members 208A-B, with horizontally-oriented legs 228A-B contacting segments 136 and 140 of base plate 14. As illustrated in FIGS. 3A-D, brackets 204A-B may be one- or multi-piece and may have complex shape if desired. Such complex shapes may especially be useful if seat track 10 is to be tested, as no vertical member would be present for clamping. Instead, clamping would occur solely by positioning base plate 14 between brackets 204A-B and clamping members 208A-B.

FIGS. 4A-D detail alternative system 300 comprising clamp blocks 304A-B and clamp devices 308A-B. Clamp blocks 304A-B may be connected directly to load cell 26. Holes 312 may be made in segments 136 and 140 of base plate 14, and holes 316 may be present in clamp devices 308A-B. Fasteners 320 may then pass through corresponding holes 312 and 316 to fix the position of base plate 14 relative to load cell 26.

FIGS. 5A-D depict alternative system 400. System 400 includes central clamping members 404A-B secured directly to load cell 26 (preferably using countersunk bolts). Secondary clamping members 408A-B attach to, respectively, central clamping members 404A-B and provide support surfaces for base plate 14. Clamp devices 412A-B may then sandwich base plate 14, with fasteners 416 passing through openings 420 of the clamp devices 412A-B and openings 424 made in base plate 14 so as to be received by openings 428 of secondary clamping members 408A-B.

FIGS. 6A-D, finally, show alternative system 500 of the present invention. System 500 is generally similar to system 100, although it may include fasteners 504 passing through openings 508 in vertical member 74 of seat track 70. If vertical member 74 is not present, clamping of segments 136 and 140 may continue to occur.

The foregoing is provided for purposes of illustrating, explaining, and describing exemplary embodiments and certain benefits of the present invention. Modifications and adaptations to the illustrated and described embodiments will be apparent to those skilled in the relevant art and may be made without departing from the scope or spirit of the invention. Additionally, although systems and methods described herein are designed principally for testing of components relating to aircraft seats, any or all of them may relate to other seats (vehicular or otherwise) or be used for other purposes as appropriate or desired.

What is claimed is:

1. A method of mounting a seat track to a test fixture, comprising:
   a. providing a seat track comprising a vertical member and a base plate having an upper surface and a bottom surface, wherein the vertical member extends downwardly from the bottom surface of the base plate;
   b. clamping the vertical member with at least one clamping member, wherein the clamping member is beneath the base plate;
   c. providing a load cell as the test fixture below the base plate and the vertical member;
   d. connecting the at least one clamping member to the test fixture;
   e. contacting the upper surface of the base plate with at least one bracket, wherein one end of the bracket is mounted on the base plate;
   f. connecting the other end of the bracket to the at least one clamping member;
   g. contacting the base plate with at least one rectangular section on the bottom surface of the base plate so that the base plate is clamped between the at least one bracket and the at least one rectangular section; and
   h. clamping the base plate between one end of a second bracket and a second rectangular section and connecting the other end of the second bracket to the test fixture.

2. A method according to claim 1 in which the seat track has a generally "T"-shaped cross section.

3. A method according to claim 1 in which the seat track has a generally "I"-shaped cross-section.

4. A method of mounting a seat track to a test fixture without needing to form any holes in the track, comprising:
   a. providing a seat track comprising:
      i. a base plate having an upper surface and a lower surface and defining a longitudinal axis;
      ii. a vertical member extending below the base plate along the longitudinal axis;
   b. providing a load cell as the test fixture;
   c. connecting first and second clamping members to the test fixture with the vertical member positioned between the first and second clamping members;
   d. contacting the upper surface of the base plate with one end of each of first and second brackets;
   e. contacting the lower surface of the base plate with first and second rectangular sections; and
   f. connecting the other end of the first bracket to the first clamping member and the other end of the second bracket to the second clamping member so that the base plate is clamped between the first bracket and the first rectangular section and between the second bracket and the second rectangular section.

* * * * *

UNITED STATES PATENT AND TRADEMARK OFFICE
CERTIFICATE OF CORRECTION

PATENT NO. : 7,628,370 B2  Page 1 of 1
APPLICATION NO. : 11/480789
DATED : December 8, 2009
INVENTOR(S) : Morel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 323 days.

Signed and Sealed this

Second Day of November, 2010

David J. Kappos
*Director of the United States Patent and Trademark Office*